US007777001B2

(12) United States Patent
Fasano et al.

(10) Patent No.: US 7,777,001 B2

(45) Date of Patent: Aug. 17, 2010

(54) AGONIST POLYPEPTIDE OF RECEPTOR FOR ZOT AND ZONULIN

(75) Inventors: Alessio Fasano, West Friendship, MD (US); Stefanie N. Vogel, Columbia, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 632 days.

(21) Appl. No.: 11/502,490

(22) Filed: Aug. 11, 2006

(65) Prior Publication Data

US 2006/0276403 A1 Dec. 7, 2006

Related U.S. Application Data

(62) Division of application No. 10/891,492, filed on Jul. 15, 2004, now Pat. No. 7,294,689.

(60) Provisional application No. 60/487,889, filed on Jul. 15, 2003.

(51) Int. Cl.
*A61K 38/12* (2006.01)

(52) U.S. Cl. ..................................................... 530/329

(58) Field of Classification Search ....................... None
See application file for complete search history.

(56) References Cited

U.S. PATENT DOCUMENTS

| | | | | |
|---|---|---|---|---|
| 5,665,389 | A | 9/1997 | Fasano | |
| 5,827,534 | A | 10/1998 | Fasano | |
| 5,864,014 | A * | 1/1999 | Fasano | 530/350 |
| 5,908,825 | A | 6/1999 | Fasano et al. | |
| 5,912,323 | A | 6/1999 | Fasano | |
| 5,945,510 | A | 8/1999 | Fasano | |
| 5,948,629 | A | 9/1999 | Fasano | |
| 6,355,270 | B1 * | 3/2002 | Ferrari et al. | 424/489 |
| 6,458,925 | B1 | 10/2002 | Fasano | |
| 6,670,448 | B2 | 12/2003 | Fasano | |
| 7,026,294 | B2 | 4/2006 | Fasano et al. | |
| 2002/0123047 | A1 | 9/2002 | Burnham | |

FOREIGN PATENT DOCUMENTS

| | | | |
|---|---|---|---|
| WO | WO-01/89551 | A1 | 11/2001 |
| WO | WO-03/066859 | A2 | 8/2003 |

OTHER PUBLICATIONS

Jonson et al, "A Critical View on Conservative Mutations," Protein Engineering (2001), vol. 14, pp. 397-401.*

Berendsen (H..J.C. Berendsen. A Glimpse of the Holy Grail? Science (1998) vol. 282, pp. 642-643.*

Fasano "Modulation of Intestinal permeability: an innovative method of oral drug delivery for the treatment of inherited and acquired human diseases," Molecular Genetics and Metabolism 64, 12-18 (1998).*

W. Wang et al. "Human zonulin, a potential modulator of intestinal tight junctions" JnI, of Cell Sciences, vol. 113, pp. 4435-4440 (2000).

A. Fasano, "Modulation of Intestinal Permeability: An Innovative Method of Oral Drug Delivery for the Treatment of Inherited and Acquired Human Diseases" Molecular Genetics and Metabolism, vol. 64, pp. 12-18 (1998).

PCT International Search Report for PCT/US04/22753.

Uzzau, S. et al., "Expression of 'vibrio cholerae zonula occludens toxin and analysis of its subcellular localization", Microb. Pathog., vol. 27, No. 6, Dec. 1999, pp. 377-385 (Abstract only).

Salama, N. N. et al., "The effect of DeltaG on the transport and oral absorption of macromolecules", J. Pharm. Sci., vol. 93, No. 5, May 2004, pp. 1309-1310 (Abstract only).

Salama, N. N. et al., "Effect of the biologically active fragment of zonula occludens toxin, delta G, on the intestinal paracellular transport and oral absorption of mannitol", Int. J. Pharm. Sci., vol. 251, No. 1-2, Jan. 2003, pp. 113-121 (Abstract only).

Ikeda, O. et al., "Expression of proteinase-activated receptor-2 in human pancreatic cancer: a possible relation to cancer invasion and induction of fibrosis", Int. J. Oncol., vol. 2, Feb. 2003, pp. 295-300 (Abstract only).

Frungieri, M. B. et al., "Proliferative action of mast-cell tryptase is mediated by PAR2, COX2, prostaglandins, and PPARy: Possible relevance to human fibrotic disorders", PNAS, vol. 99, No. 23, Nov. 12, 2002, pp. 15072-15077.

Baudry, B. et al., "Cloning of a Gene (zot) Encoding a New Toxin Produced by *Vibrio cholerae*", Infection of Immunity, vol. 60, No. 2, Feb. 1992, pp. 428-434.

Di Pierro, M. et al., "Zonula Occludens Toxin Structure-Function Analysis", J. Bio. Chem.., vol. 276, No. 22, Jun. 1, 2001, pp. 19160-19165.

Fasano, A. et al., "*Vibrio cholerae* produces a second enterotoxin, which affects intestinal tight junctions", Proc. Natl. Acad. Sci. USA, vol. 88, Jun. 1991, pp. 5242-5246.

El Asmar, R. et al., "Host-Dependent Zonulin Secretion Causes the Impairment of the Small Intestine Barrier Function After Bacterial Exposure", Gastroenterology, vol. 123, No. 5, 2002, pp. 1607-1615.

Lu, R. et al., "Affinity Purification and Partial Characterization of the Zonulin/Zonula Occludents Toxin (Zot) Receptor from Human Brain", J. Neurochem., vol. 74, No. 1, 2000, pp. 320-326.

Uzzau, S. et al., "Purification and preliminary characterization of the zonula occludens toxin receptor from human (CaCo2) and murine (IEC6) intestinal cell lines", FEMS Microbiology Letters, vol. 194, 2001, pp. 1-5.

* cited by examiner

*Primary Examiner*—Cecilia Tsang
*Assistant Examiner*—Thomas S Heard

(57) ABSTRACT

Agonist polypeptide of a receptor protein has been identified. The agonist can be used to facilitate drug and antigen absorption. Suitable routes of administration include oral, nasal, transdermal, and intravenous. Pharmaceutical formulations may comprise a therapeutic agent or an immunogenic agent in combination with the agonist polypeptide.

10 Claims, 8 Drawing Sheets

AGONIST POLYPEPTIDE OF RECEPTOR FOR ZOT AND ZONULIN

This application is a divisional application of U.S. patent application Ser. No. 10/891,492, filed Jul. 15, 2004, currently pending, which claims priority to U.S. provisional patent application Ser. No. 60/487,889, filed Jul. 15, 2003, the disclosures of which are specifically incorporated herein by reference.

STATEMENT REGARDING FEDERALLY SPONSORED RESEARCH

The invention was made with U.S. government support under NIH grant numbers DK48373 and AI18797. The U.S. government has certain rights in the invention

TECHNICAL FIELD OF THE INVENTION

Background of the Invention

Intestinal tight junction dysfunction occurs in a variety of clinical conditions, including food allergies, infections of the gastrointestinal tract, autoimmune diseases, and inflammatory bowel diseases (42). Healthy, mature gut mucosa with its intact tight junction serves as the main barrier to the passage of macromolecules. During the healthy state, small quantities of immunologically active antigens cross the gut host barrier. These antigens are absorbed across the mucosa through at least two pathways. The vast majority of absorbed proteins (up to 90%) crosses the intestinal barrier via the transcellular pathway, followed by lysosomal degradation that converts proteins into smaller, non-immunogenic peptides. These residual peptides are transported as intact proteins, through the paracellular pathway; it involves a subtle but sophisticated regulation of intercellular tight junction that leads to antigen tolerance. When the integrity of the tight junction system is compromised, as with prematurity or after exposure to radiation, chemotherapy, and/or toxins, a deleterious immune response to environmental antigens (including autoimmune diseases and food allergies) may be elicited. There is a continuing need in the art to diagnose and treat such diseases and conditions. There is a continuing need in the art to identify new drugs for treating such diseases.

Several microorganisms exert an irreversible cytopathic effect on epithelial cells that impacts cytoskeletal organization and tight junction function. These bacteria alter intestinal permeability either directly (i.e., EPEC) or through the elaboration of toxins (e.g., *Clostridium difficile, Bacteroides fragilis*) (43). The *Vibrio cholerae* phage CXTΦ ZOT protein mimics the human protein zonulin and exploits the physiological mechanisms of tight junction regulation. Zot possesses multiple domains that allow a dual function of the protein as a morphogenetic phage peptide for the *Vibrio cholerae* phage CTXΦ and as an enterotoxin that modulates intestinal tight junctions. Zot action is mediated by a cascade of intracellular events that lead to a PKCα-dependent polymerization of actin microfilaments strategically localized to regulate the paracellular pathway (38). The toxin exerts its effect by interacting with the surface of enteric cells. Zot binding varies within the intestine, being detectable in the jejunum and distal ileum, decreasing along the villous-crypt axis, and not being detectable in the colon (44). This binding distribution coincides with the regional effect of Zot on intestinal permeability (44) and with the preferential F-actin redistribution induced by Zot in the mature cells of the villi (38).

SUMMARY OF THE INVENTION

A first embodiment of the invention is an agonist polypeptide of a human receptor of zonulin and *Vibrio cholerae* phage CTXϕ ZOT protein. The agonist polypeptide comprises amino acid sequence FCIGRL (SEQ ID NO: 4). The polypeptide is less than 100 amino acid residues in length.

A second embodiment of the invention is a pharmaceutical composition for treating a disease. The composition comprises a therapeutic agent for treating the disease and an agonist polypeptide of a human receptor of zonulin and *Vibrio cholerae* phage CTXϕ ZOT protein. The agonist polypeptide comprises amino acid sequence FCIGRL (SEQ ID NO: 4). The polypeptide is less than 100 amino acid residues in length.

A third embodiment of the invention is a method of delivering a therapeutic agent to a target tissue. A therapeutic agent for treating a disease and an agonist polypeptide of a human receptor of zonulin and *Vibrio cholerae* phage CTXϕ ZOT protein is administered to a patient with the disease. The agonist polypeptide comprises amino acid sequence FCIGRL (SEQ ID NO: 4). The polypeptide is less than 100 amino acid residues in length.

A fourth embodiment of the invention is a method of delivering a therapeutic agent to a target tissue. A therapeutic agent for treating a disease and an agonist polypeptide of a human receptor of zonulin and *Vibrio cholerae* phage CTXϕ ZOT protein are administered via the nose of a patient who has the disease. The agonist polypeptide comprises amino acid sequence FCIGRL (SEQ ID NO: 4). The polypeptide is less than 100 amino acid residues in length.

A fifth embodiment of the invention is a method of delivering a therapeutic agent to a target tissue. A therapeutic agent for treating a disease and an agonist polypeptide of a human receptor of zonulin and *Vibrio cholerae* phage CTXϕ ZOT protein are administered via the mouth of a patient who has the disease. The agonist polypeptide comprises amino acid sequence FCIGRL (SEQ ID NO: 4). The polypeptide is less than 100 amino acid residues in length.

A sixth embodiment of the invention is a method of delivering a therapeutic agent to a target tissue. A therapeutic agent for treating a disease and an agonist polypeptide of a human receptor of zonulin and *Vibrio cholerae* phage CTXϕ ZOT protein are administered via the skin of a patient who has the disease. The agonist polypeptide comprises amino acid sequence FCIGRL (SEQ ID NO: 4). The polypeptide is less than 100 amino acid residues in length.

A seventh embodiment of the invention is a method of delivering a therapeutic agent to a target tissue. A therapeutic agent for treating a disease and an agonist polypeptide of a human receptor of zonulin and *Vibrio cholerae* phage CTXϕ ZOT protein are administered via the blood of a patient who has the disease. The agonist polypeptide comprises amino acid sequence FCIGRL (SEQ ID NO: 4). The polypeptide is less than 100 amino acid residues in length.

An eighth embodiment of the invention is a method for identifying or purifying a human receptor of Zonulin and *V. cholerae* phage CTXϕ Zot. A sample comprising one or more proteins is contacted with an antibody under conditions suitable for antibody antigen binding. The antibody is raised against amino acids SLIGKVDGTSHVTG as shown in SEQ ID NO: 5. Proteins in the sample not bound to the antibody are removed. Proteins bound to the antibody are identified as a human receptor of Zonulin and Zot or as forming a preparation enriched for said receptor.

A ninth embodiment of the invention is a method of screening for drug candidates for treating a disease. A first human protein identified by antibody SAM11 is contacted with a second protein selected from the group consisting of *V. cholerae* phage CTXϕ Zot, human Zonulin, and MyD88. The contacting is performed separately in the presence and in the absence of a test substance. The amount of the first protein bound to the second protein in the presence of test substance is compared to the amount bound in the absence of test substance. A test substance is identified as a drug candidate if it decreases the amount of first protein bound to second protein.

A tenth embodiment of the invention is a vaccine composition for inducing an immune response. The vaccine comprises an immunogenic agent for inducing an immune response and an agonist of a human receptor of zonulin and *Vibrio cholerae* phage CTXϕ ZOT protein. The agonist polypeptide comprises amino acid sequence FCIGRL (SEQ ID NO: 4). The polypeptide is less than 100 amino acid residues in length.

An eleventh embodiment of the invention is a method of diagnosing an autoimmune disease in a patient. A first body sample from the patient is contacted with an antibody raised against amino acids SLIGKVDGTSHVTG as shown in SEQ ID NO: 5. Amount of the antibody bound by the first body sample is compared to an amount bound by a second body sample of a healthy control who does not have an autoimmune disease. An auto-immune disease is identified in the patient if the first body sample binds more of the antibody than the second.

A twelfth embodiment of the invention is a method of treating a patient with increased expression of zonulin relative to a control healthy individual. An antibody raised against amino acids SLIGKVDGTSHVTG as shown in SEQ ID NO: 5, is administered to the patient. Symptoms of the disease are thereby alleviated.

A thirteenth embodiment of the invention is an antibody which is raised against amino acids SLIGKVDGTSHVTG as shown in SEQ ID NO: 5. The antibody binds to a protein expressed in CaCo2 cells that co-localizes with a protein bound by synthetic inhibitor peptide FZ1/0 (as shown in SEQ ID NO: 3). The antibody does not bind to human or rat cells that express a recombinant human PAR-2. The antibody is not SAM11.

A fourteenth embodiment of the invention is an antibody which binds to a protein expressed in CaCo2 cells that co-localizes with a protein bound by synthetic inhibitor peptide FZ1/0 (as shown in SEQ ID NO: 3). The antibody does not bind to human or rat cells that express a recombinant human PAR-2. The antibody is not SAM11.

A fifteenth embodiment of the invention is an agonist polypeptide of a human receptor of zonulin and *Vibrio cholerae* phage CTXϕ ZOT protein. The agonist polypeptide comprises a sequence selected from the group consisting of $Xaa_1$ Cys Ile Gly Arg Leu (SEQ ID NO: 7), Phe $Xaa_2$ Ile Gly Arg Leu (SEQ ID NO: 8), Phe Cys $Xaa_3$ Gly Arg Leu (SEQ ID NO: 9), Phe Cys Ile $Xaa_4$ Arg Leu (SEQ ID NO: 10), Phe Cys Ile Gly $Xaa_5$ Leu (SEQ ID NO: 11), and Phe Cys Ile Gly Arg $Xaa_6$ (SEQ ID NO: 12). The polypeptide is less than 100 amino acid residues in length. $Xaa_1$ is selected from the group consisting of Ala, Val, Leu, Ile, Pro, Trp, Tyr, and Met; $Xaa_2$ is selected from the group consisting of Gly, Ser, Thr, Tyr, Asn, and Gln; $Xaa_3$ is selected from the group consisting of Ala, Val, Leu, Ile, Pro, Trp, and Met; $Xaa_4$ is selected from the group consisting of Gly, Ser, Thr, Tyr, Asn, Ala, and Gln; $Xaa_5$ is selected from the group consisting of Lys and His; $Xaa_6$ is selected from the group consisting of Ala, Val, Leu, Ile, Pro, Trp, and Met.

A sixteenth embodiment of the invention is an agonist polypeptide of a human receptor of zonulin and *Vibrio cholerae* phage CTXϕ ZOT protein. The agonist polypeptide comprises a sequence selected from the group consisting of: $Xaa_1$ $Xaa_2$ Ile Gly Arg Leu (SEQ ID NO: 13), $Xaa_1$ Cys $Xaa_3$ Gly Arg Leu (SEQ ID NO: 14), $Xaa_1$ Cys Ile $Xaa_4$ Arg Leu (SEQ ID NO: 15), $Xaa_1$ Cys Ile Gly $Xaa_5$ Leu (SEQ ID NO: 16), $Xaa_1$ Cys Ile Gly Arg $Xaa_6$ (SEQ ID NO: 17), Phe $Xaa_2$ $Xaa_3$ Gly Arg Leu (SEQ ID NO: 18), Phe $Xaa_2$ Ile $Xaa_4$ Arg Leu (SEQ ID NO: 19), Phe $Xaa_2$ Ile Gly $Xaa_5$ Leu (SEQ ID NO: 20), Phe $Xaa_2$ Ile Gly Arg $Xaa_6$ (SEQ ID NO: 21), Phe Cys $Xaa_3$ $Xaa_4$ Arg Leu (SEQ ID NO: 22), Phe Cys $Xaa_3$ Gly $Xaa_5$ Leu (SEQ ID NO: 23), Phe Cys $Xaa_3$ Gly Arg $Xaa_6$ (SEQ ID NO: 24), Phe Cys Ile $Xaa_4$ $Xaa_5$ Leu (SEQ ID NO: 25), Phe Cys Ile $Xaa_4$ Arg $Xaa_6$ (SEQ ID NO: 26), and Phe Cys Ile Gly $Xaa_5Xaa_6$ (SEQ ID NO: 27). The polypeptide is less than 100 amino acid residues in length. $Xaa_1$ is selected from the group consisting of Ala, Val, Leu, Ile, Pro, Trp, Tyr, and Met; $Xaa_2$ is selected from the group consisting of Gly, Ser, Thr, Tyr, Asn, and Gln; $Xaa_3$ is selected from the group consisting of Ala, Val, Leu, Ile, Pro, Trp, and Met; $Xaa_4$ is selected from the group consisting of Gly, Ser, Thr, Tyr, Asn, Ala, and Gln; $Xaa_5$ is selected from the group consisting of Lys and His; $Xaa_6$ is selected from the group consisting of Ala, Val, Leu, Ile, Pro, Trp, and Met.

These and other embodiments which will be apparent to those of skill in the art upon reading the specification provide the art with reagents and methods for treating diseases, diagnosing diseases, and discovering drugs.

DETAILED DESCRIPTION OF THE INVENTION

Figures 1A, 1B:
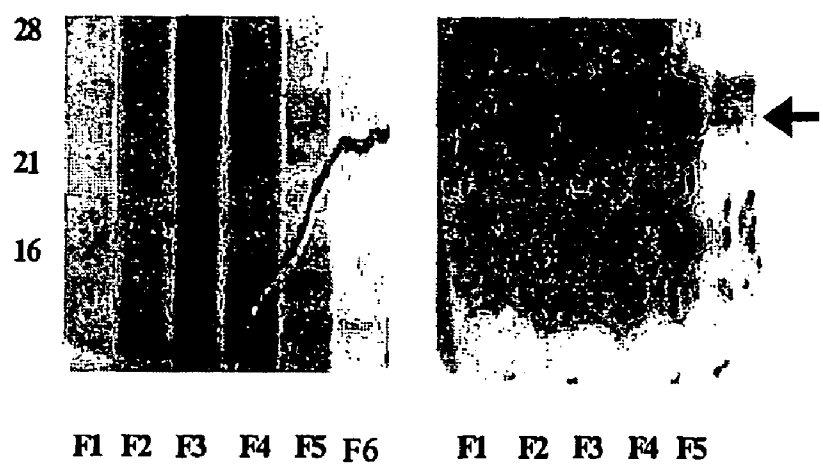
FIGS. 1A and 1B Comassie (FIG. 1A) and Western immunoblotting (FIG. 1B) of the six HPLC fractions obtained from intestinal tissue lysates. The zonulin-positive fraction F5 showed a ~23 kDa that was not present in the other five fractions.
Figures 2A, 2B:
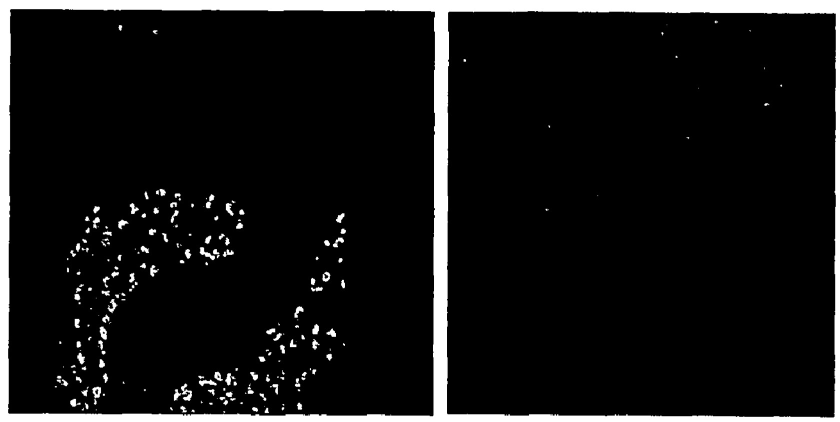
FIGS. 2A and 2B. In situ immunofluorescence microscopy of rat small intestines exposed to either fluoresceinated FZI/0 (FIG. 2A) or FZI/1 (FIG. 2B). Note the fluorescence distribution at the upper third of the villi where the Zot/zonulin receptor was originally described (see ref. 44).

The inventors have developed an agonist polypeptide of a human receptor of zonulin and *Vibrio cholerae* phage CTXϕ ZOT protein. The polypeptide comprises amino acid sequence FCIGRL (SEQ ID NO: 4). The polypeptide is less than 100 amino acid residues, or less than 50, 40, 30, 20, 10, or 8 amino acid residues. The polypeptide may contain only the six amino acids FCIGRL (SEQ ID NO: 4), or it may have additional amino acids. The other amino acids may provide other functions, e.g., antigen tags, for facilitating purification.

The agonist polypeptide can be used to facilitate absorption of therapeutic or immunogenic agents. The agonist polypeptide facilitates absorption across the intestine, the blood-brain barrier, the skin, and the nasal mucosa. Thus the agonist polypeptide can be formulated with or co-administered with a therapeutic or immunogenic agent which targets the intestine, the brain, the skin, the nose. A pharmaceutical composition according to the present invention need not be pre-mixed prior to administration, but can be formed in vivo when two agents are administered within 24 hours of each other. Preferably the two agents are administered within 12, 8, 4, 2, or 1 hours of each other.

Therapeutic agents according to the invention are any which can be used to treat a human or other mammal. The agent can be for example, an antibody or an antibody fragment (such as an Fab, $F(ab')_2$, a single chain antibody (ScFv)), an anti-cancer drug, an antibiotic, a hormone, or a cytokine. The therapeutic agent can be one which acts on any organ of the body, such as heart, brain, intestine, or kidneys. Diseases which may be treated according to the invention include, but are not limited to food allergies, gastrointestinal infection, autoimmune disease, inflammatory bowel disease, Celiac Disease, gastrointestinal inflammation.

Intravenous dosage compositions for delivery to the brain are well-known in the art. Such intravenous dosage compositions generally comprise a physiological diluent, e.g., distilled water, or 0.9% (w/v) NaCl.

A "nasal" delivery composition differs from an "intestinal" delivery composition in that the latter must have gastroresistent properties in order to prevent the acidic degradation of the active agents (e.g., zonulin receptor agonist and the therapeutic agent) in the stomach, whereas the former generally comprises water-soluble polymers with a diameter of about 50 μm in order to reduce the mucociliary clearance, and to achieve a reproducible bioavailability of the nasally administered agents. An "intravenous" delivery composition differs from both the "nasal" and "intestinal" delivery compositions in that there is no need for gastroresistance or water-soluble polymers in the "intravenous" delivery composition.

The mode of administration is not critical to the present. The mode of administration may be oral, for intestinal delivery; intranasal, for nasal delivery; and intravenous for delivery through the blood-brain barrier. Other modes of administration as are known in the art may also be used, including, but not limited to intrathecal, intramuscular, intrabronchial, intrarectal, intraocular, and intravaginal delivery.

Oral dosage compositions for small intestinal delivery are well-known in the art. Such oral dosage compositions may comprise gastroresistent tablets or capsules (Remington's Pharmaceutical Sciences, 16th Ed., Eds. Osol, Mack Publishing Co., Chapter 89 (1980); Digenis et al, J. Pharm. Sci., 83:915-921 (1994); Vantini et al, Clinica Terapeutica, 145: 445-451 (1993); Yoshitomi et al, Chem. Pharm. Bull., 40:1902-1905 (1992); Thoma et al, Pharmazie, 46:331-336 (1991); Morishita et al, Drug Design and Delivery, 7:309-319 (1991); and Lin et al, Pharmaceutical Res., 8:919-924 (1991)); each of which is incorporated by reference herein in its entirety).

Tablets are made gastroresistent by the addition of, e.g., either cellulose acetate phthalate or cellulose acetate terephthalate.

Capsules are solid dosage forms in which the biologically active ingredient(s) is enclosed in either a hard or soft, soluble container or shell of gelatin. The gelatin used in the manufacture of capsules is obtained from collagenous material by hydrolysis. There are two types of gelatin. Type A, derived from pork skins by acid processing, and Type B, obtained from bones and animal skins by alkaline processing. The use of hard gelatin capsules permit a choice in prescribing a single biologically active ingredient or a combination thereof at the exact dosage level considered best for the individual subject. The hard gelatin capsule typically consists of two sections, one slipping over the other, thus completely surrounding the biologically active ingredient. These capsules are filled by introducing the biologically active ingredient, or gastroresistent beads containing the biologically active ingredient, into the longer end of the capsule, and then slipping on the cap. Hard gelatin capsules are made largely from gelatin, FD&C colorants, and sometimes an opacifying agent, such as titanium dioxide. The USP permits the gelatin for this purpose to contain 0.15% (w/v) sulfur dioxide to prevent decomposition during manufacture.

Oral dosage compositions for small intestinal delivery also include liquid compositions which may optionally contain aqueous buffering agents that prevent the therapeutic agent and agonist polypeptide from being significantly inactivated by gastric fluids in the stomach, thereby allowing the biologically active ingredient and agonist polypeptide to reach the small intestines in an active form. Examples of such aqueous buffering agents which can be employed in the present invention include bicarbonate buffer (pH 5.5 to 8.7, preferably about pH 7.4).

When the oral dosage composition is a liquid composition, it is preferable that the composition be prepared just prior to administration so as to minimize stability problems. In this case, the liquid composition can be prepared by dissolving lyophilized therapeutic agent and agonist polypeptide in the aqueous buffering agent.

Nasal dosage compositions for nasal delivery are well-known in the art. Such nasal dosage compositions generally comprise water-soluble polymers that have been used extensively to prepare pharmaceutical dosage forms (Martin et al, In: Physical Chemical Principles of Pharmaceutical Sciences, 3rd Ed., pages 592-638 (1983)) that can serve as carriers for peptides for nasal administration (Davis, In: Delivery Systems for Peptide Drugs, 125:1-21 (1986)). The nasal absorption of peptides embedded in polymer matrices has been shown to be enhanced through retardation of nasal mucociliary clearance (Illum et al, Int. J. Pharm., 46:261-265 (1988)). Other possible enhancement mechanisms include an increased concentration gradient or decreased diffusion path for peptides absorption (Ting et al, Pharm. Res., 9:1330-1335 (1992)). However, reduction in mucociliary clearance rate has been predicted to be a good approach toward achievement or reproducible bioavailability of nasally administered systemic drugs (Gonda et al, Pharm. Res., 7:69-75 (1990)). Microparticles with a diameter of about 50 μm are expected to deposit in the nasal cavity (Bjork et al, Int. J. Pharm., 62:187-192 (1990)); and Illum et al, Int. J. Pharm., 39:189-199 (1987), while microparticles with a diameter under 10 μm can escape the filtering system of the nose and deposit in the lower airways. Microparticles larger than 200 μm in diameter will not be retained in the nose after nasal administration (Lewis et al, Proc. Int. Symp. Control Rel. Bioact. Mater., 17:280-290 (1990)).

The particular water-soluble polymer employed is not critical to the present invention, and can be selected from any of the well-known water-soluble polymers employed for nasal dosage forms. A typical example of a water-soluble polymer useful for nasal delivery is polyvinyl alcohol (PVA). This material is a swellable hydrophilic polymer whose physical properties depend on the molecular weight, degree of hydrolysis, cross-linking density, and crystallinity (Peppas et al, In: Hydrogels in Medicine and Pharmacy, 3:109-131 (1987)). PVA can be used in the coating of dispersed materials through phase separation, spray-drying, spray-embedding, and spray-densation (Ting et al, supra).

A "skin" delivery composition of the invention may include in addition to a therapeutic or immunogenic agent, fragrance, creams, ointments, colorings, and other compounds so long as the added component does not deleteriously affect transdermal delivery of the therapeutic or immunogenic agent. Conventional pharmaceutically acceptable emulsifiers, surfactants, suspending agents, antioxidants, osmotic enhancers, extenders, diluents and preservatives may also be added. Water soluble polymers can also be used as carriers.

The particular therapeutic or immunogenic agent employed is not critical to the present invention, and can be, e.g., any drug compound, biologically active peptide, vaccine, or any other moiety otherwise not absorbed through the transcellular pathway, regardless of size or charge.

Examples of drug compounds which can be employed in the present invention include drugs which act on the cardiovascular system, drugs which act on the central nervous system, antineoplastic drugs and antibiotics. Examples of drugs which act on the cardiovascular system which can be employed in the present invention include lidocaine, adenosine, dobutamine, dopamine, epinephrine, norepinephrine and phentolamine. Others as are known in the art can also be used.

Examples of drugs which act on the central nervous system which can be employed in the present invention include doxapram, alfentanil, dezocin, nalbuphine, buprenorphine, naloxone, ketorolac, midazolam, propofol, metacurine, mivacurium and succinylcholine. Others as are known in the art can also be used.

Examples of antineoplastic drugs which can be employed in the present include cytarabine, mitomycin, doxorubicin, vincristine and vinblastine. Others as are known in the art can also be used.

Examples of antibiotics which can be employed in the present include methicillin, mezlocillin, piperacillin, cetoxitin, cefonicid, cefmetazole and aztreonam. Others as are known in the art can also be used.

Examples of biologically active peptides which can be employed in the present invention include hormones, lymphokines, globulins, and albumins. Examples of hormones which can be employed in the present invention include testosterone, nandrolene, menotropins, insulin and urofolltropin. Others as are known in the art can also be used. When the biologically active ingredient is insulin, the oral dosage composition of the present invention is useful for the treatment of diabetes. Examples of lymphokines which can be employed in the present invention include interferon-α, interferon-β, interferon-γ, interleukin-1, interleukin-2, interleukin-4 and interleukin-8.

Examples of globulins which can be employed in the present invention include α-globulins, β-globulins and γ-globulins (immunoglobulin). Examples of immunoglobulins which can be employed in the present invention include polyvalent IgG or specific IgG, IgA and IgM, e.g., anti-tetanus antibodies. An example of albumin which can be employed in the present invention is human serum albumin. Others as are known in the art can also be used.

Examples of vaccines which can be employed in the present invention include peptide antigens and attenuated microorganisms and viruses. Examples of peptide antigens which can be employed in the present invention include the B subunit of the heat-labile enterotoxin of enterotoxigenic *E. coli*, the B subunit of cholera toxin, capsular antigens of enteric pathogens, fimbriae or pili of enteric pathogens, HIV surface antigens, dust allergens, and acari allergens. Others as are known in the art can also be used.

Examples of attenuated microorganisms and viruses which can be employed in the present invention include those of enterotoxigenic *Escherichia coli*, enteropathogenic *Escherichia coli, Vibrio cholerae, Shigella flexneri, Salmonella typhi* and rotavirus (Fasano et al, In: Le Vaccinazioni in Pediatria, Eds. Vierucci et al, CSH, Milan, pages 109-121 (1991); Guandalini et al, In: Management of Digestive and Liver Disorders in Infants and Children, Elsevior, Eds. Butz et al, Amsterdam, Chapter 25 (1993); Levine et al, Sem. Ped. Infect. Dis., 5:243-250 (1994); and Kaper et al, Clin. Micrbiol. Rev., 8:48-86 (1995), each of which is incorporated by reference herein in its entirety).

The amount of therapeutic or immunogenic agent employed is not critical to the present invention and will vary depending upon the particular ingredient selected, the disease or condition being treated, as well as the age, weight and sex of the subject being treated.

The amount of ZOT receptor agonist polypeptide employed is also not critical to the present invention and will vary depending upon the age, weight and sex of the subject being treated. Generally, the final concentration of ZOT receptor agonist polypeptide employed in the present invention to enhance absorption of the biologically active ingredient by the intestine is in the range of about $10^{-5}$ M to $10^{-10}$ M, preferably about $10^{-6}$ M to $5.0\times10^{-5}$ M. To achieve such a final concentration in the intestine, the amount of ZOT receptor agonist polypeptide in a single oral dosage composition of the present invention will generally be about 4.0 ng to 1000 ng, preferably about 40 ng to 80 ng.

The ratio of therapeutic or immunogenic agent to ZOT receptor agonist polypeptide employed is not critical to the present invention and will vary depending upon the amount of biologically active ingredient to be delivered within the selected period of time. Generally, the weight ratio of therapeutic or immunogenic agent to ZOT receptor agonist polypeptide employed in the present invention is in the range of about 1:10 to 3:1, preferably about 1:5 to 2:1.

Antibodies which bind to the protein identified by an antibody raised against amino acids SLIGKVDGTSHVTG (SEQ ID NO: 5) can be used diagnostically, therapeutically, and as a research tool. One such antibody is SAM11, which is available from Zymed Laboratories, South San Francisco, Calif. Other such antibodies can be readily made using standard techniques for raising monoclonal or polyclonal antibodies. Upregulation of zonulin receptors in diseases can be detected using the SAM11 antibodies or other antibodies that bind to the same human protein. The antibodies can be conjugated to a diagnostically detectable label. For therapeutic uses the antibody can be conjugated to a therapeutic or toxic agent, including radionuclides, anti-neoplastic agents, etc.

The identification of binding partners for the zonulin and Zot receptor protein permits one to assay for test substances which disrupt the binding. Binding partners identified to date include MyD88, zonulin, Zot, and ΔG. Any assay for binding of two proteins can be used. These can be in vitro or in vivo assays. The assays may employ antibodies or solid phase binding substrates. Any such assay as is known in the art can be used.

Conservative substitutions, in which an amino acid is exchanged for another having similar properties, can be made in the agonist polypeptide having the sequence of SEQ ID NO: 4. Examples of conservative substitutions include, but are not limited to, Gly⇆Ala, Val⇆Ile⇆Leu, Asp⇆Glu, Lys⇆Arg, Asn⇆Gln, and Phe⇆Trp⇆Tyr. Conservative amino acid substitutions typically fall in the range of about 1 to 2 amino acid residues. Guidance in determining which amino acid residues can be substituted without abolishing biological or immunological activity can be found using computer programs well known in the art, such as DNASTAR software, or in Dayhoff et al. (1978) in *Atlas of Protein Sequence and Structure* (Natl. Biomed. Res. Found., Washington, D.C.).

Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Particularly preferred oligopeptide analogs include substitutions that are conservative in nature, i.e., those substitutions that take place within a family of amino acids that are related in their side chains. Specifically, amino acids are generally divided into families: (1) acidic—aspartate and glutamate; (2) basic—lysine, arginine, histidine; (3) non-polar—alanine, valine, leucine, isoleucine, proline, phenylalanine, methionine, tryptophan; (4) uncharged polar—glycine, asparagine, glutamine, cysteine, serine threonine, and tyrosine; and (5) aromatic amino acids—phenylalanine, tryptophan, and tyrosine. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity.

Any assay known in the art can be used to determine ZOT receptor agonist biological activity. For example, the assay may involve (1) assaying for a decrease of tissue resistance (Rt) of ileum mounted in Ussing chambers as described by Fasano et al, *Proc. Natl. Acad. Sci., USA,* 8:5242-5246 (1991); (2) assaying for a decrease of tissue resistance (Rt) of intestinal epithelia cell monolayers in Ussing chambers as described below; or (3) assaying for intestinal or nasal enhancement of absorption of a therapeutic or immunogenic agent, as described in WO 96/37196; U.S. patent application Ser. No. 08/443,864, filed May 24, 1995; U.S. patent application Ser. No. 08/598,852, filed Feb. 9, 1996; and U.S. patent application Ser. No. 08/781,057, filed Jan. 9, 1997.

Agonists of ZOT receptor will rapidly open tight junctions in a reversible and reproducible manner, and thus can be used as intestinal or nasal absorption enhancers of a therapeutic or immunogenic agent in the same manner as ZOT is used as intestinal or nasal absorption enhancers, as described in WO 96/37196; U.S. patent application Ser. No. 08/443,864, filed May 24, 1995; U.S. patent application Ser. No. 08/598,852, filed Feb. 9, 1996; and U.S. patent application Ser. No. 08/781,057, filed Jan. 9, 1997.

Antibodies to the zot/zonulin receptor can be used as anti-inflammatory agents for the treatment of gastrointestinal inflammation that gives rise to increased intestinal permeability. Thus, the antibodies of the present invention are useful, e.g., in the treatment of intestinal conditions that cause protein losing enteropathy. Protein losing enteropathy may arise due to: infection, e.g., *C. difficile* infection, enterocolitis, shigellosis, viral gastroenteritis, parasite infestation, bacterial overgrowth, Whipple's disease; diseases with mucosal erosion or ulcerations, e.g., gastritis, gastric cancer, collagenous colitis, inflammatory bowel disease; diseases marked by lymphatic obstruction, e.g., congenital intestinal lymphangiectasia, sarcoidosis-lymphoma, mesenteric tuberculosis, and after surgical correction of congenital heart disease with Fontan's operation; mucosal diseases without ulceration, e.g., Menetrier's disease, celiac disease, eosinophilic gastroenteritis; and immune diseases, e.g., systemic lupus erythematosus or food allergies, primarily to milk (see also Table 40-2 of Pediatric Gastrointestinal Disease Pathophysiology Diagnosis Management, Eds. Wyllie et al, Saunders Co. (1993), pages 536-543; which is incorporated by reference herein in its entirety). The antibodies can be administered to patients with cancer, autoimmune disease, vascular disease, bacterial infection, Celiac Disease, asthma, and irritable bowel syndrome.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Rat small intestinal tissues were analyzed by a combination of gel filtration chromatography and zonulin ELISA. Rat intestine homogenates were loaded on a sephacryl column (length 90 cm, diameter 2.6, cm calibrated with standard molecular weight markers) and fractions collected and analyzed by zonulin ELISA to determine zonulin concentrations. Of six fractions (F1-F6) tested, F5 contained the highest zonulin concentrations. Each fraction was resolved by SDS-PAGE, transferred, and immunoblotted with zonulin-immunoreactive, anti-Zot antibodies (FIG. 1B). Western analysis revealed two major bands that migrated with approximate apparent Mr of 24,000 and 23,000 in the zonulin-positive fraction, F5, while the zonulin-negative fractions, F1-4,6, each revealed only one immunoreactive band (~24 kDa). Therefore, the ~23 kDa band from F5 (see arrow FIG. 1B) was excised from a Comassie blue-stained gel and subjected to Matrix Assisted Laser Desorption Ionization (MALDI) mass spectrometry. Search using the Profound search engine for protein matches (domain name 129.85.19.192, directory profound_bin; program WebProFound.exe?FORM=1) revealed a high similarity of this protein (estimate Z score 1.58) with the rat mast cell protease II 1). Mast cell proteases are serine proteinases contained in mast cell granules with trypsin-like (tryptase) and chymotrypsin-like (chymase) properties (46). Mucosal mast cells (MMC) contain predominantly protease II (MCP-II), whereas connective tissue mast cells contain mainly protease I (46). MCP-II is particularly abundant in the pulmonary and gastrointestinal (47) mucosa. In the gastrointestinal tract, one of the better-characterized bioactivities of MCP-II is the modulation of mucosal epithelial permeability following nematode infestation (48). In vitro studies suggest that MCP-II opens the epithelial barrier by disrupting the tight junction complex. Therefore, our proposed hypothetical model for the zonulin system and the established functions of MCP-II are remarkably compatible. However, we detected major differences between zonulin and MCP-II, including their sources (zonulin is present in enterocytes (49) and macrophages) and the stimuli for their release (intestinal worm infestation for MCP-II [48] and bacteria and gliadin [49] for zonulin).

We performed microsnapwell experiments in WBB6/F1-W/Wv mice that possess pleiotropic defects in germ cells, RBC's and mucosal mast cells and, therefore, lack MCP-II (55). Tissues mounted in the microsnapwell system and exposed at increasing time intervals (up to 3 h) to zonulin-releasing stimuli showed a TEER decrease (−170±15.8 Omhs/cm2 versus −43±11 of untreated tissues) and a parallel increase in zonulin release (10.0±0.8 ng/mg protein vs 0.2±0.7 in untreated tissues) similar to that observed in wild type animals (−120±20 and 15.1±3.1, respectively).

Taken together, our data suggest that zonulin is distinct from MCP-II and may represent one of several physiologic activators of PAR-2 or a variant of PAR-2. Pancreatic trypsin is the most efficient activator of PAR-2, but there is a discrepancy between the availability of pancreatic trypsin and the distribution of PAR-2 (47). Biologically active trypsin is present in the lumen of the small intestine, where it may activate PAR-2 at the apical membrane of enterocytes (47), but PAR-2 is also found in many tissues where it must be activated by an as yet identified physiological activator (50). Zonulin represents a strong candidate for such a PAR-2 activator and may reconcile this apparent discrepancy, since it has been isolated both in intestinal and extraintestinal tissues (51).

Example 2

We have previously demonstrated that Zot binds to the surface of rabbit intestinal epithelium and that this binding varies along the different regions of the intestine (44). The binding distribution coincides with the regional effect of Zot on intestinal permeability and with the preferential F-actin redistribution induced by Zot in the mature cells of the villi (38, 44). To further characterize the Zot receptor, we performed the following experiments.

A. Binding Experiments

Binding experiments were performed with several epithelial cell lines, including IEC6 (rat, intestine), CaCo2 (human, villous-like enterocytes), T84 (human, crypt-like enterocytes), MDCK (canine, kidney), and bovine pulmonary artery (BPA) endothelial cells. For immunofluorescence analysis, confluent monolayers ($2.0\times10^5$) on glass slides were incubated for increasing time intervals (5 min, 30 min, 60 min), at 4° C. or 37° C. with $5\times10^{-9}$ M Zot or a negative control. Following incubation of monolayers with Zot (0.2 μM) for 15 min at 37° C., cells were washed 10 times with cold PBS, suspended and lysed. Cell lysates were resolved by SDS-PAGE, transferred to PVDF membranes, and probed with anti-Zot antibodies. To establish the specificity of Zot binding radiolabeled Zot was used. These experiments were performed in the absence or presence of either 10- or 50-fold molar excess of cold unlabeled Zot. When incubated with Zot protein for increasing time intervals, CaCo2 and IEC6 intestinal epithelial cells as well as endothelial cells displayed binding on the cell surface, as compared to cells exposed to the negative control. In contrast, no staining was observed on either T84 or MDCK cells after incubation for up to 60 min with His-Zot. The cell-specificity of Zot binding was confirmed by immunoblotting analysis. Zot bound to IEC6, CaCo2, and BPA but not to T84 and MDCK cells.

B. Purification of Zot-Binding Protein.

A His-Zot affinity column was prepared by immobilizing overnight, at room temperature, 1.0 mg of purified His-Zot to a pre-activated gel (Aminolink, Pierce). The column was washed with PBS, and then loaded with a crude cell lysate obtained using 106 of either IEC6 cells or CaCo2 cells. After a 90-min incubation at room temperature, the column was washed five times with 14 ml of PBS, and the proteins which bound to His-Zot were eluted from the column with 4.0 ml of 50 mM glycine (pH 2.5), 150 mM NaCl, and 0.1% (v/v) Triton X-100. The pH of the 1.0 ml eluted fractions was immediately neutralized with 1.0 N NaOH. Collected fractions were subjected to 6.0-15.0% (w/v) gradient SDS-PAGE under reducing conditions. The resolved proteins were transferred to a nitrocellulose membrane and subjected to NH2-terminal microsequencing using a Perkin-Elmer Applied Biosystems Apparatus Model 494. The eluted fractions obtained from both IEC6 and CaCo2 cells contained a single protein band with an apparent Mr of 66 kDa as observed by SDS-PAGE under reducing conditions. Treatment with neuraminidase reduced the size of the putative Zot receptor to 35 kDa, suggesting that this receptor is sialylated (51).

C. Characterization of the Zot/Zonulin Receptor.

Our recent data suggesting that zonulin is structurally similar to mast cell protease (MCP)-II has led us to hypothesize that the Zot/zonulin receptor could be similar, if not identical, to the MCP-II proteinase-activated receptor (PAR-2). PAR-2 has several characteristics in common with those that we have described for the Zot/zonulin receptor. Specifically, mature PAR-2 is a glycoprotein of 68-80 kDa that is reduced to 36-40 kDa by deglycosylation (47). Similarly, the Zot/zonulin receptor has a molecular mass of 66 kDa that is reduced by deglycosylation to 35 kDa (51). Distribution of PAR-2 within the gastrointestinal tract (47) coincides with the Zot/zonulin receptor distribution in the gut (44). PAR-2 intracellular signaling involves activation of phospholipase C (PLC), protein kinase C (PKC) (52), and actin polymerization leading to cytoskeletal rearrangement (53). Zot and zonulin activate these same intracellular signaling pathways through a common intestinal surface receptor (38). Similarly to the Zot/zonulin effect in the gut, activation of intestinal PAR-2 results in increased intestinal permeability (54). Finally, PAR-2 is activated by cleavage of its extracellular domain by trypsin, creating a new N-terminus that acts as a "tethered ligand". Exogenous addition of the peptide SLIGRL (PAR-2 AP), that corresponds to the proteolytically activated, newly created N-terminus, also activates PAR-2 independently of receptor cleavage (52). The N-terminus of the 12 kDa, biologically active Zot fragment (ΔG) encompasses the Zot extracellular domain (aa residues 288-399) that is proteolytically cleaved by *Vibrio cholerae* in the intestinal tract of the host. The ΔG N-terminus contains a peptide (FCIGRL amino acids 288-293) that is structurally similar to the agonist ligand motif of PAR-2. To define more precisely the structural requirements for engagement and activation of the target receptor, two ΔG mutants were synthesized by mutating either the putative PAR-2 binding motif (ΔG291) or the region just downstream from the ligand motif (ΔG298). These peptides were compared to ΔG for their capacity to bind to IEC-6 cells as well as for their biological activity on rat small intestine mounted in Ussing chambers. IEC6 cells incubated with ΔG291 (G291V) showed reduced binding to IEC6 cells as compared to cells incubated with ΔG, while no binding was observed on cells incubated with the ΔG298 peptide (G298V). Biological assays in Ussing chambers showed that ΔG291 had a residual, but not a statistically significant effect on tj disassembly, while ΔG298 failed to elicit any detectable permeating effect. These results paralleled the effects obtained with these two mutants in the binding assay and suggested that the G residue in position 291 and, most importantly, the G residue in 298 may play crucial roles in ΔG binding and activation of its target receptor, possibly through changes in the protein configuration. Currently, one of the major limitations in studying the PAR-2 functions under both physiologic and pathologic circumstances is the lack of specific PAR-2 inhibitors (52). Based on our structure-function analyses, we designed a synthetic octapeptide (corresponding to Zot amino acid residues 291-298) that encompasses the two G residues that we targeted for mutagenesis, but lacking the first 3 amino acid residues (288-290) of the putative ligand motif. This synthetic peptide, FZI/0, was tested on ileal tissue mounted in Ussing chambers either alone or in combination with Zot, ΔG, or zonulin. No changes in tissues Rt exposed to either FZI/0 or to the scrambled octapeptide (FZI/1) were observed. Treatment of ileal tissues with FZI/0 prior to and throughout the study period prevented the Rt changes in response to Zot, ΔG, and zonulin while the permeating effect of the three proteins was unaffected by pretreatment with FZI/1. These data strengthen our hypothesis that Zot and zonulin target the same receptor and suggest that FZI/0 may exert its inhibitory effect by binding to, but not activating, this receptor. To test this last hypothesis, we performed in situ binding experiments using rat small intestine incubated with either fluoresceinated FZI/0 or FZI/1. Tissue exposed to FZI/0 showed numerous florescent particles, while no signal was detected in tissues incubated with FZI/1.

Example 3

Figures 3A, 3B, 3C:
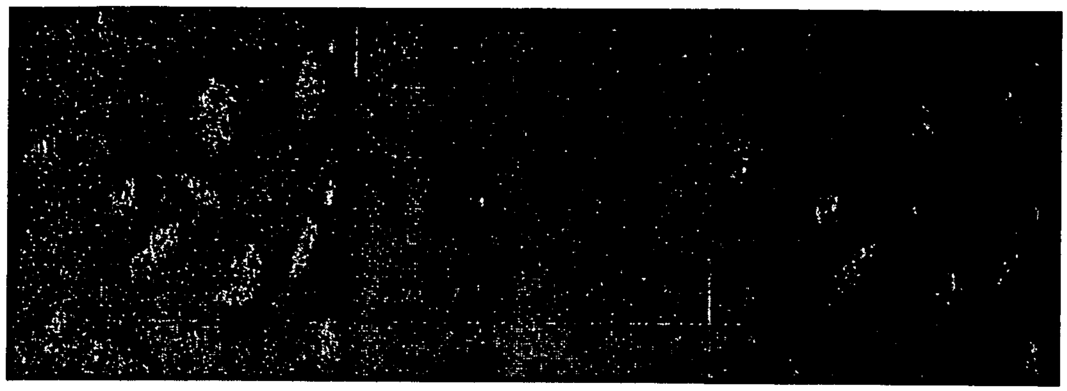
FIG. 3A to 3C. PAR-2-FZI/0 colocalization. Caco 2 cells were immunostained with either FITC-FZI/0 (FIG. 3A) or mouse anti-human PAR2 monoclonal antibodies (FIG. 3B). Overlapping of the two images (FIG. 3C) showed a co-localization of PAR-2 and FZI/0 immunofluorescent particles.

The Zot/zonulin synthetic inhibitor FZI/0 binds to PAR-2. To establish whether FZI/0 binds to PAR-2, double label, co-localization immuno-fluorescence microscopy was performed in Caco2 cell monolayers. Briefly, cells were incubated for increasing time intervals with either FITC-FZI/0 or with mouse monoclonal anti-human PAR-2 antibodies, followed by incubation with rhodamine-labeled anti-mouse IgG antibodies. Cells were then washed 3 times with PBS, fixed in 3.7% paraformaldehyde in PBS (pH 7.4) for 15 min at room temperature, the cover slips were mounted with glycerol-PBS (1:1) at pH 8.0 and analyzed with fluorescence microscopy (ZEISS). Immunofluorescent particles were visualized in both FITC-FZI/0- and anti-PAR-2 antibodies-exposed cells (FIG. 3). Overlapping of the two images showed colocalization of the PAR-2 receptor and FZI/0 was evident (FIG. 3).

Example 4

Figures 4A, 4B, 4C, 4D:
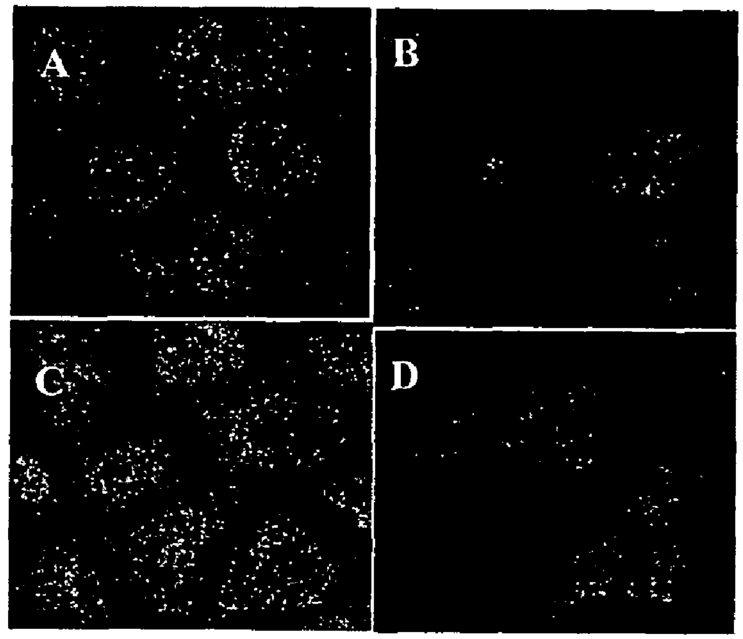
FIGS. 4A-4D. FZI/0-PAR-2 AP competitive binding experiments. Caco2 cells exposed to FITC-labelled FZI/0 (FIG. 4B) showed a significant number of fluorescent particles compared to the cells exposed to media control (FIG. 4A). An excess of PAR2-AP (100×) displaced FZI/0 (FIG. 4C), while 100× of a scrambled peptide did not (FIG. 4D).

FZI/0—PAR-2 AP competitive binding experiments. The activation of PAR-2 requires binding of either its tryptase-generated, cleaved N-terminal portion or the synthetic peptide equivalent, PAR-2 AP, to the receptor's extracellular loop 2 (ECL2) (47). To establish whether FZI/0 binds to the same receptor domain, competitive binding experiments were conducted in Caco2 cells. Cell monolayers were incubated with FITC-FZI/0 ($2\times10^{-8}$M)) either in the presence of an excess of PAR-2 AP ($10^{-6}$M) or a scrambled peptide and then analyzed by fluorescence microscopy. Cells exposed to an excess of PAR-2 AP showed a significant reduction of FZI/0 immunofluorescent staining particles compared to monolayers exposed to the scrambled peptide (FIG. 4), suggesting that FZI/0 binds to PAR-2 and can be competitively displaced by PAR-2 AP.

Figures 5A, 5B, 5C, 5D:
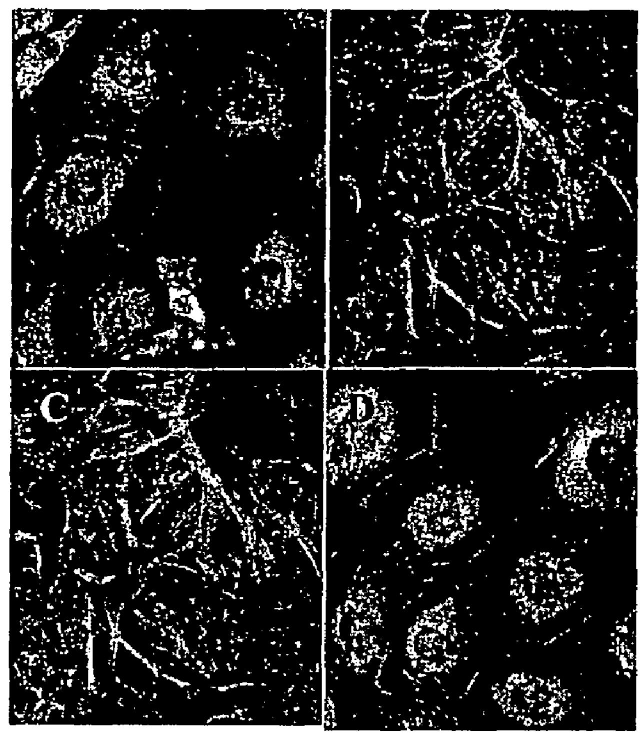
FIGS. 5A to 5D. Actin cytoskeleton arrangement in Caco2 cells exposed to PAR2-AP (FIG. 5A), BSA (FIG. 5B), PAR2-AP+FZI/0 (FIG. 5C), or PAR-2 AP+FZI/1 (FIG. 5D).

Effect of the Zot/zonulin inhibitor FZI/0 on PAR-2 AP-induced actin rearrangement. It has been recently reported that activation of PAR-2 receptor by PAR-2 AP promotes cytoskeletal reorganization (53). To establish whether this effect can be prevented by the synthetic Zot/zonulin peptide inhibitor, FZI/0, immunofluorescence studies were conducted in Caco2 cell monolayers. Cells exposed to $10^{-6}$M PAR-2 AP (FIG. 5A) displayed dissolution of stress fibers whereas BSA-treated monolayers did not (FIG. 5B). These cytoskeletal changes were blocked by the pre-incubation with $2\times10^{-6}$M FZI/0 (FIG. 5C), but not by the scrambled peptide FZI/1 (FIG. 5D). Therefore, PAR-2 AP and FZI/0 appear to bind to the identical structure on enterocytes.

Example 5

Figures 6A, 6B:
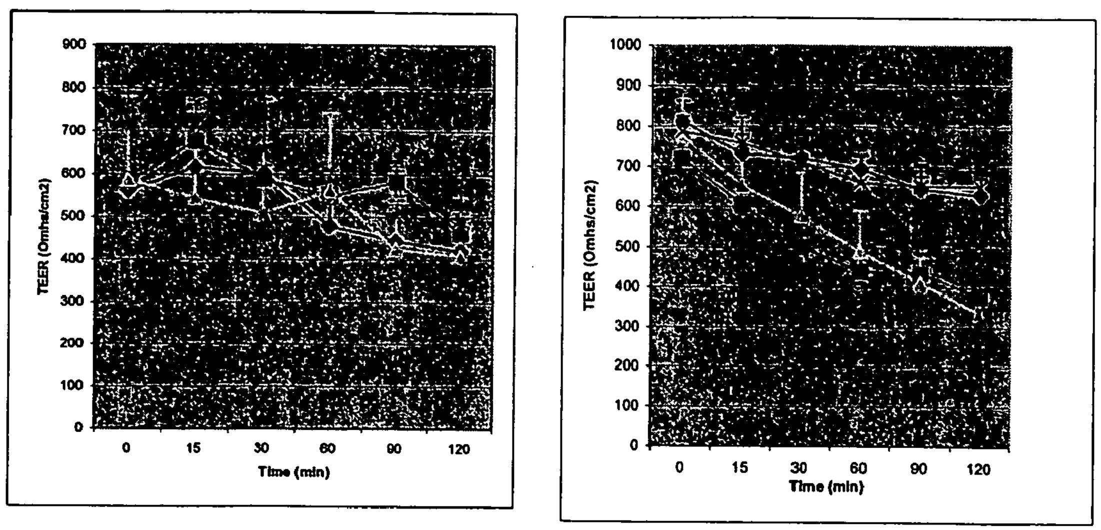
FIGS. 6*a* to 6B. Effect of MCP-II (FIG. 6A) and PAR-2 AP (FIG. 6B) on mouse intestinal TEER. Both MCP-II (○) and PAR-2 AP (Δ) induced significant drops in TEER compared to control tissues (◇). These changes were comparable to ΔG-induced changes (■) and were completely prevented by preincubation with FZI/0 (x).

Effect of PAR-2 AP and MCP-II on intestinal permeability. PAR-2 is highly expressed on the apical membrane of enterocytes and, presumably, regulates one or more enteric cell functions (52). We asked whether one of these functions could be the zonulin-mediated regulation of intestinal permeability in response to bacterial colonization. To explore this hypothesis, we tested the effect of both MCP-II and PAR-2 AP treatment on mouse intestinal small intestine in the micro-snapwell assay. Addition of $10^{-6}$M PAR-2 AP or MCP-II ($10^{-8}$M) to the luminal aspect of the intestine decreased TEER compared to untreated tissues and this PAR2-dependent decrement was completely prevented by pretreatment with FZI/0 (FIG. 6). These results provide one more line of evidence to support the hypothesis that PAR-2 is the target receptor for both Zot and zonulin and suggests that this receptor is also involved in the regulation of intercellular tight junctions.

Example 6

Figures 7A, 7B:
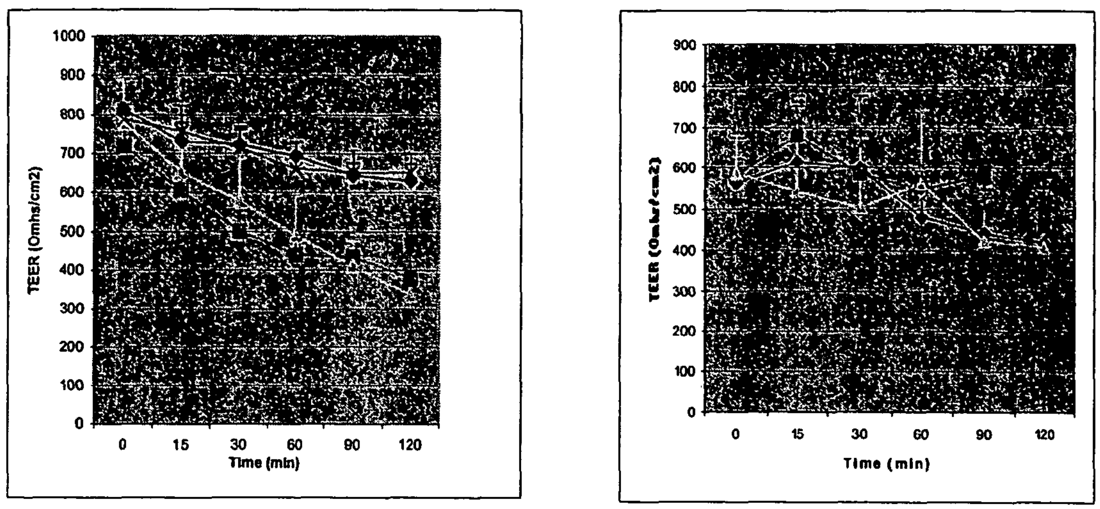
FIG. 7A to 7B. Effect of PAR-2 AP on intestinal TEER in wild type (FIG. 7A) and MyD88 KO (FIG. 7B) mice. In wild type mice, both PAR-2 AP (Δ) and ΔG (■) induced significant drops in TEER compared to control tissues (◇) that were completely prevented by preincubation with FZI/0 (x). No TEER changes were observed in MyD88 KO mice under any treatment conditions.

Involvement of MyD88 in PAR-2 signaling. Many microbial structures, such as bacterial lipopolysaccharide or the fusion protein from Respiratory Syncytial Virus, as well as certain endogenous proteins, activate the cells of the innate immune system through intracytoplasmic signaling that is initiated by Toll-like receptors (TLRs; 55). To date, ten mammalian TLRs have been identified. Within the intracytoplasmic domains of TLRs and the Interleukin-1 and Interleukin-18 receptors, is a region of homology that is referred to as the "Toll-IL-1 Receptor" or "TIR" domain. The TIR domain is responsible for binding critical adaptor molecules such as Myeloid Differentiation Factor 88 (MyD88). The striking similarity of signaling pathways engaged by PAR-2 activation and those engaged by TLRs (e.g., NF-κB, etc.; 52) led us to hypothesize that zot/zonulin might engage a member of the TLR family or a closely related protein. Therefore, we tested the capacity of Zot and PAR-2 AP to induce changes in intestinal transepithelial electrical resistance (TEER) was tested in wild-type mice and in mice that have a targeted mutation (knockout, KO) in the MyD88 gene (FIGS. 7A and 7B). The data in FIG. 7A indicate that both PAR-2 AP and ΔG induce a comparable drop in intestinal resistance over time in wild-type tissues, which was reversed by preincubation with the inhibitory zot peptide, FZI/0. In contrast, intestinal tissues derived from MyD88 knockout mice failed to respond to either stimulus to exhibit a decrease in TEER.

Figure 8:
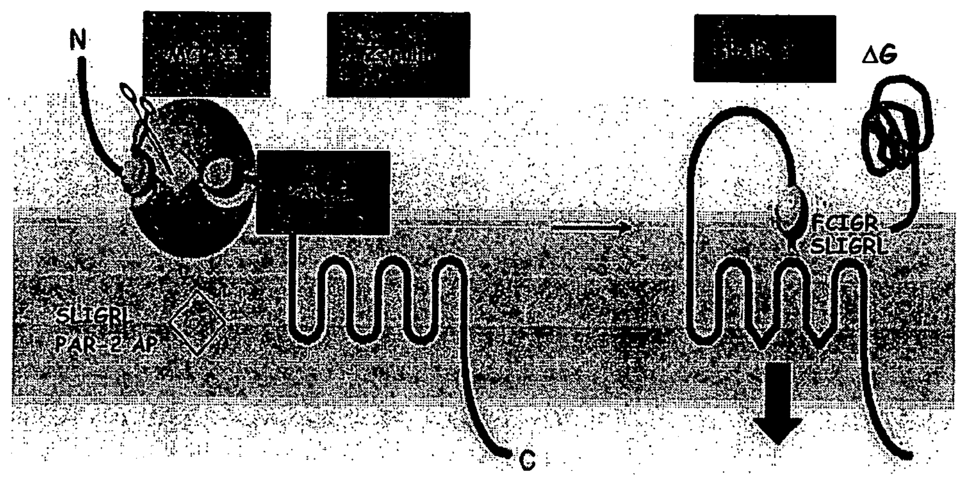
FIG. 8. Proposed activation of receptor by Zot and zonulin. As a MCP-II analogue, zonulin activates the receptor by cleaving its N-terminus, while Zot directly binds and activates the receptor via its PAR-2 AP-homologous N-terminal motif. The activation of PAR-2 by MCP-II and PAR-2 AP or the activation of the zonulin receptor by zonulin and ΔG is blocked by the competitive binding inhibitor FZI/0.

Taken together, these results suggest that Zot and zonulin activate the same receptor (a PAR-2 variant or homolog), possibly through two distinct mechanisms (FIG. 8). Our data support the notion that Zot binds directly to the PAR-2 (variant or homolog) ECL2 and activates the receptor signaling, while zonulin, as a MCPII analogue, may activate the target receptor by cleaving it at its N-terminus (FIG. 8). Moreover, we propose that PAR-2 (variant or homolog) may directly engage MyD88 through a TIR-like domain.

REFERENCES

1. Anderson, J M and Van Itallie, C M. 1995. Tight junctions and the molecular basis for regulation of paracellular permeability. *Am. J. Physiol.* 269:467-475.
2. Cereijido, M. 2001. Evolution of ideas on the tight junction. In Tight Junctions, CRC Press, Inc. Boca Raton, Fla. 1-18.
3. Fasano, A., Baudry B., Pumplin, D W, Wasserman S S, Tall B D, Ketley J., and Kaper, J B. 1991. *Vibrio cholerae* produces a second enterotoxin, which affects intestinal tight junctions. *Proc. Natl. Acad. Sci. USA.* 88:5242-5246.
4. Baudry, B. Fasano A., Ketley J M, and Kaper, J B. 1992. Cloning of a gene (zot) encoding a new toxin produced by *Vibrio cholerae. Infect. Immun.* 60:428-434.
5. Diamond J M. The epithelial junction: bridge, gate and fence. 1977. *Physiologist* 20: 10-18.
6. Madara J L. Loosing Tight Functions Lessons from the Intestine. 1989. *J. Clin. Invest.* 83: 1089-1094.
7. Madara J L, and Dharmsathaphorn. 1985. Occluding junction structure-function relationships in a cultured epithelial monolayer. *J. Cell Biol.* 101:2124-2133.
8. Magnuson T, Jacobson J B, and Stackpole C W. 1978. Relationship between intercellular permeability and junction organization in the preimplantation mouse embryo. *Dev. Biol.* 67:214-224.
9. Revel J P, and Brown S S. 1976. Cell junctions in development with particular reference to the neural tube. *Cold Spring Harbor Symp. Quant. Biol.* 40:443-455.
10. Schneeberger E E, Walters D V, and Olver R E. 1978. Development of intercellular junctions in the pulmonary epithelium of the foetal lamb. *J. Cell Sci.* 32:307-324.
11. Gilula N B, Fawcett D W, and Aoki A. 1976. The sertoli cell occluding junctions and gap junctions in mature and developing mammalian testis. *Dev. Biol.* 50:142-168.
12. Madara J L, and Pappenheimer J R. 1987. Structural basis for physiological regulations of paracellular pathways in intestinal epithelia. *J. Membr. Biol.* 100:149-164.
13. Mazariegos M R, Tice L W, and Hand A R. 1984. Alteration of tight junctional permeability in the rat parotid gland after isoproteranol stimulation. *J. Cell Biol.* 98:1865-1877.
14. Sardet C, Pisam M, and Maetz J. 1979. The surface epithelium of teleostean fish gills. Cellular and junctional adaptations of the chloride cell in relation to salt adaptation. *J. Cell Biol.* 80:96-117.
15. Milks L C, Conyers G P, and Cramer E B. 1986. The effect of neutrophil migration on epithelial permeability. *J. Cell Biol.* 103:2729-2738.
16. Nash S, Stafford J, and Madara J L. 1988. The selective and superoxide-independent disruption of intestinal epithelial tight junctions during leukocyte transmigration. *Lab. Invest.* 59:531-537.
17. Shasby D M, Winter M, and Shasby S S. 1988. Oxidants and conductance of cultured epithelial cell monolayers: inositol phospholipid hydrolysis. *Am. J. Physiol.* 255 (*Cell Physiol.* 24):C781-C788.
18. Furuse, M., Hirase, M., Itoh, M., Nagafuchi, A., Yonemura, S., Tsukita, Sa., and Tsukita, Sh. 1993. Occludin: a novel integral membrane protein localizing at tight junctions. *J. Cell Biol,* 123:1777-1788.
19. Furuse Mikio, F. K., Hiiragi Takashi, Fujimoto Kazushi, Tsukita Shoichiro. 1998. Claudin-1 and -2: Novel integral membrane proteins localizing at tight junctions with no sequence similarity to occludin. *J Cell Biol.* 141: 1539-1550.
20. Martin-Padura, I., Lostgalio, S, Schneemann, M., Williams, L., Romano, M., Fruscella, P., Panzeri, C., Stoppacciaro, A., Ruco, L., Vill, A., Simmons, D., and Dejana, E. 1998. Junctional Adhesion Molecule, a Novel Member of the Immunoglobulin Superfamily That Distributes at Intercellular Junctions and Modulates Monocyte Transmigration. *J Biol Chem* 142:117-127.
21. Bazzoni, G., Martinez-Estrada O., Orsenigo, F., Cordenonsi, M., Citi, S., and Dejana, E. 2000. Interaction of Junctional Adhesion Molecule with the Tight Junction Components, ZO-1, Cingulin, and Occludin *J Biol Chem* 275: 20520-20526.
22. Mitic L. L., Van Itallie C. M. 2001. Occludin and claudins: transmembrane proteins of the tight junction. In Tight Junctions, CRC Press, Inc., Boca Raton, Fla. 213-230.
23. Furuse M., Sasaki H., Tsukita S. 1999. Manner of interaction of heterogeneous claudin species within and between tight junction strands. J Cell Biol, 147:891-903.
24. Citi S. 2001. The cytoplasmic plaque proteins of the tight junction. In Tight Junctions, CRC Press, Inc., Boca Raton, Fla. 231-264.
25. Stevenson B R, Anderson J M, and Bullivant S. 1988. The epithelial tight junction: Structure, function and preliminary biochemical characterization. *Molec. Cell Biochem.* 83:129-145.
26. Anderson, J M 1996. Cell signalling: MAGUK magic. *Curr. Biol.* 6:382-384
27. Citi S, Sabannay H, Jakes R, Geiger B, and Kendrich-Jones J. 1988. Cingulin, a new peripheral component of tight junctions. *Nature* (London) 333:272-275.
28. Zahraoui A., Joberty G, Arpin M., Fontaine J J., Hellio R, Tavitian A., and Louvard D. 1994. A small rab GTPase is distributed in cytoplasmic vesicles in non polarized cells but colocalized with the tight junction marker Zo-1 in polarized epithelial cells. *J. Cell Biol.* 124:101-115.
29. Denker B M, Saha, C, Khawaja, S, and Nigam, S K. 1996. Involvement of a heterotrimeric G protein a subunit in tight junction biogenesis. *J. Biol. Chem.* 271:25750-25753.
30. Dodane, V., and Kachar, B. 1996. Identification of isoforms of G proteins and PKC that colocalize with tight junctions. *J. Membr. Biol.* 149:199-209.
31. Keon B H, Schafer, S, Kuhn, C, Grund, C, and W W Franke. 1996. Symplekin, a novel type of tight junction plaque protein. *J. Cell Biol.* 134:1003-1018.
32. Gottardi C J, Arpin, M, Fanning A S, and Louvard D. 1996. The junction-associated protein, zonula occludens-1, localizes to the nucleus before the maturation and during the remodeling of cell-cell contacts. *Proc. Natl. Acad. Sci. USA* 93:10779-84.
33. Gumbiner B. 1987. Structure, biochemistry, and assembly of epithelial tight junctions. *Am. J. Physiol.* 253:C749-C758.
34. Madara J L, Barenberg D, and Carlson S. 1986. Effects of Cytochalasin D on Occluding Junctions of Intestinal Absorptive Cells: Further Evidence That the Cytoskeleton May Influence Paracellular Permeability and Junctional Charge Selectivity. *J. Cell Biol.* 102: 2125-2136.3
35. Drenchahn D, and Dermietzel R. 1988. Organization of the Actin Filament Cytoskeleton in the Intestinal Brush Border: A Quantitative and Qualitative Immunoelectron Microscope Study. *J. Cell Biol.* 107:1037-1048.

36. Hecht F. et al. 1996. Expression of the catalytic domain of myosin light chain kinase increases paracellular permeability. *Am. J. Physiol.* 271:C1678-1684.

37. Tsuneo K., Brauneis U., Gatmaitan Z., and Arias, I. 1991. Extracellular ATP, intracellular calcium and canalicular contraction in rat hepatocyte doublets. *Hepatology.* 14:640-647.

38. Fasano A., Fiorentini C, Donelli G., Uzzau S, Kaper J B, Margaretten K., Ding, X, Guandalini S. Comstock L, Goldblum S E. 1995. Zonula Occludens Toxin Modulates Tight Junctions through Protein Kinase C-dependent Actin Reorganization, In Vitro. *J. Clinical Invest.* 96:710-720.

39. Itoh M., Furuse M., Morita K., Kubota K., Saitou M., Tsukita S. 1999. Direct binding if three tight junction-associated MAGUKs, ZO-1, ZO-2, and ZO-3, with the COOH termini of claudins. *J Cell Biol* 147:1351-1363.

40. Benais-Pont G., Matter K., Balda M. S. 2001. Intracellular signaling in classical and new tight junction functions. In Tight Junctions, CRC Press, Inc., Boca Raton, Fla. 367-394.

41. W. Wang, R. Lu, M. G. Clemente, A. Fasano. Zonulin and its prokaryotic analogue *Vibrio cholerae*-derived Zonula occludens toxin (Zot) share the same mechanism of action on intercellular tight junctions. *Ped Res* (in revision).

42. Fasano A. 2001. Pathological and therapeutical implications of macromolecule passage through the tight junction. In Tight Junctions, CRC Press, Inc., Boca Raton, Fla. 697-722.

43. Hecht G. 2001. Microbial pathogens that affect tight junctions. In Tight Junctions, CRC Press, Inc., Boca Raton, Fla. 493-515.

44. A. Fasano, S. Uzzau, C. Fiore, K. Margaretten. 1997. The Enterotoxic Effect of Zonula Occludens Toxin (Zot) on Rabbit Small Intestine Involves the Paracellular Pathway. *Gastroenterology;* 112:839-846.

45. Marcial M. A., Carlson S. L., Madara J. L. 1984. Partitioning of paracellular conductance along the ileal crypt-villus axis: a hypothesis based on structural analysis with detailed consideration of tight junction structure-function relationships. *J Membr Biol,* 80:59-70.

46. H. R. P. Miller, A. D. Pemberton. Tissue-specific expression of mast cell granule serine proteinases and their role in inflammation of the lung and gut. *Immunology,* 105:275-390.

47. S. Gibson, A. Mackeller, G. F. J. Newlands, H. R. P. Miller. 1987. Phenotype expression of mast cell granule proteinases. Distribution of mast cell proteinase I and II in the rat digestive system. Immunology, 62:621-627.

48. S. J. King, R. P. Miller. 1984. Anaphylactic release of mucosal mast cell protease and its relationship to gut permeability in *Nippostrongylus*-primed rats. *Immunology,* 51:653-660.

49. M. G. Clemente, S. De Virgiliis, J. S. Kang, R. Macatagney, M. Congia, A. Fasano. 2003. New insights on celiac disease pathogenesis: gliadin-induced zonulin release, actin polymerization, and early increased gut permeability. *Gut,* 52:218-223.

50. C. Cicala. 2002. Protease activated receptor 2 and the cardiovascular system. Br. J. Pharmacol, 135:14-20.

51. R. Lu, W. Wang, S. Uzzau, R. Vigorito, H. R. Zielke, A. Fasano. 2000. Affinity Purification and Partial Characterization of the Zonulin/Zonula Occludens Toxin (Zot) Receptor from Human Brain. *J. Neurochem.;* 74:320-326.

52. S. R. Macfarlane, M. J. Seatter, T. Kanke, G. D. Hunter, R. Plevin. 2001. Proteinase-activated receptors. *Pharmacol Rev* 53, 245282.

53. E. R. Sharlow, C. S. Paine, L. Babiarz, M. Eisinger, S. Shapiro, M. Seiberg. 2000. The protease-activated receptor-2 upregulates keratinocyte phagocytosis. *J Cell Sci,* 113:3093-3101.

54. N. Cenac et al. 2003. Proteinase-activated receptor-2 induced colonic inflammation in mice: possible involvement of afferent neurons, nitric oxide, and paracellular permeability. J Immunol, 170:4296-4300.

55. Dobrovolskaia M A, Vogel S N. Toll receptors, CD14, and macrophage activation and deactivation by LPS. Microbes Infect. Jul. 4, 2002; (9):903-14.

The disclosure of each reference cited is expressly incorporated herein.

We claim:

1. A method for enhancing the absorption of a therapeutic agent comprising: administering to a patient the therapeutic agent and a peptide, the peptide consisting of the amino acid sequence FCIGRL (SEQ ID NO: 4) optionally having one amino acid substitution with respect to SEQ ID NO: 4, wherein said peptide enhances the absorption of the therapeutic agent.

2. The method of claim 1, wherein the amino acid sequence is:

$Xaa_1$ Cys Ile Gly Arg Leu (SEQ ID NO: 7),

Phe $Xaa_2$ Ile Gly Arg Leu (SEQ ID NO: 8),

Phe Cys $Xaa_3$ Gly Arg Leu (SEQ ID NO: 9),

Phe Cys Ile $Xaa_4$ Arg Leu (SEQ ID NO:10),

Phe Cys Ile Gly $Xaa_5$ Leu (SEQ ID NO: 11),

Phe Cys Ile Gly Arg $Xaa_6$ (SEQ ID NO:12), wherein $Xaa_1$ is Ala, Val, Leu, Ile, Pro, Trp, Tyr, or Met; wherein $Xaa_2$ is Gly, Ser, Thr, Tyr, Asn, or Gln; $Xaa_3$ is Ala, Val, Leu, Ile, Pro, Trp, or Met; $Xaa_4$ is Gly, Ser, Thr, Tyr, Asn, Ala, or Gln; $Xaa_5$ is Lys or His; and $Xaa_6$ is Ala, Val, Leu, Ile, Pro, Trp, or Met.

3. The method of claim 1, wherein the therapeutic agent and the peptide are formulated as a pharmaceutical composition for oral delivery, the pharmaceutical composition comprising the peptide in an amount effective to enhance absorption of the therapeutic agent in the intestine.

4. The method of claim 3, wherein the pharmaceutical composition is gastroresistant.

5. The method of claim 1, wherein the therapeutic agent and the peptide are formulated as a pharmaceutical composition for nasal or pulmonary delivery.

6. The method of claim 1, wherein the therapeutic agent acts on the cardiovascular system or central nervous system.

7. The method of claim 1, wherein the therapeutic agent is a biologically active peptide.

8. The method of claim 1, wherein the therapeutic agent is a antineoplastic agent or antibiotic.

9. The method of claim 1, wherein the peptide and therapeutic agent are administered within one hour of each other.

10. A method for delivering a therapeutic agent comprising, orally administering to a patient a pharmaceutical composition comprising the therapeutic agent and a peptide in an amount effective to enhance absorption of the therapeutic agent in the intestine, the amino acid sequence of the peptide consisting of SEQ ID NO:4 optionally having one amino acid substitution with respect to SEQ ID NO:4.

* * * * *

SEQUENCE LISTING

```
<160> NUMBER OF SEQ ID NOS: 27

<210> SEQ ID NO 1
<211> LENGTH: 399
<212> TYPE: PRT
<213> ORGANISM: Vibrio Cholerae phage CTXphi

<400> SEQUENCE: 1

Met Ser Ile Phe Ile His His Gly Ala Pro Gly Ser Tyr Lys Thr Ser
 1              5                  10                  15

Gly Ala Leu Trp Leu Arg Leu Leu Pro Ala Ile Lys Ser Gly Arg His
            20                  25                  30

Ile Ile Thr Asn Val Arg Gly Leu Asn Leu Glu Arg Met Ala Lys Tyr
        35                  40                  45

Leu Lys Met Asp Val Ser Asp Ile Ser Ile Glu Phe Ile Asp Thr Asp
    50                  55                  60

His Pro Asp Gly Arg Leu Thr Met Ala Arg Phe Trp His Trp Ala Arg
65                  70                  75                  80
```

-continued

```
Lys Asp Ala Phe Leu Phe Ile Asp Glu Cys Gly Arg Ile Trp Pro Pro
                85                  90                  95

Arg Leu Thr Val Thr Asn Leu Lys Ala Leu Asp Thr Pro Pro Asp Leu
            100                 105                 110

Val Ala Glu Asp Arg Pro Glu Ser Phe Glu Val Ala Phe Asp Met His
        115                 120                 125

Arg His His Gly Trp Asp Ile Cys Leu Thr Thr Pro Asn Ile Ala Lys
    130                 135                 140

Val His Asn Met Ile Arg Glu Ala Ala Glu Ile Gly Tyr Arg His Phe
145                 150                 155                 160

Asn Arg Ala Thr Val Gly Leu Gly Ala Lys Phe Thr Leu Thr Thr His
                165                 170                 175

Asp Ala Ala Asn Ser Gly Gln Met Asp Ser His Ala Leu Thr Arg Gln
            180                 185                 190

Val Lys Lys Ile Pro Ser Pro Ile Phe Lys Met Tyr Ala Ser Thr Thr
        195                 200                 205

Thr Gly Lys Ala Arg Asp Thr Met Ala Gly Thr Ala Leu Trp Lys Asp
    210                 215                 220

Arg Lys Ile Leu Phe Leu Phe Gly Met Val Phe Leu Met Phe Ser Tyr
225                 230                 235                 240

Ser Phe Tyr Gly Leu His Asp Asn Pro Ile Phe Thr Gly Gly Asn Asp
                245                 250                 255

Ala Thr Ile Glu Ser Glu Gln Ser Glu Pro Gln Ser Lys Ala Thr Val
            260                 265                 270

Gly Asn Ala Val Gly Ser Lys Ala Val Ala Pro Ala Ser Phe Gly Phe
        275                 280                 285

Cys Ile Gly Arg Leu Cys Val Gln Asp Gly Phe Val Thr Val Gly Asp
    290                 295                 300

Glu Arg Tyr Arg Leu Val Asp Asn Leu Asp Ile Pro Tyr Arg Gly Leu
305                 310                 315                 320

Trp Ala Thr Gly His His Ile Tyr Lys Asp Thr Leu Thr Val Phe Phe
                325                 330                 335

Glu Thr Glu Ser Gly Ser Val Pro Thr Glu Leu Phe Ala Ser Ser Tyr
            340                 345                 350

Arg Tyr Lys Val Leu Pro Leu Pro Asp Phe Asn His Phe Val Val Phe
        355                 360                 365

Asp Thr Phe Ala Ala Gln Ala Leu Trp Val Glu Val Lys Arg Gly Leu
    370                 375                 380

Pro Ile Lys Thr Glu Asn Asp Lys Lys Gly Leu Asn Ser Ile Phe
385                 390                 395


<210> SEQ ID NO 2
<211> LENGTH: 397
<212> TYPE: PRT
<213> ORGANISM: Homo sapiens

<400> SEQUENCE: 2

Met Arg Ser Pro Ser Ala Ala Trp Leu Leu Gly Ala Ala Ile Leu Leu
 1               5                  10                  15

Ala Ala Ser Leu Ser Cys Ser Gly Thr Ile Gln Gly Thr Asn Arg Ser
            20                  25                  30

Ser Lys Gly Arg Ser Leu Ile Gly Lys Val Asp Gly Thr Ser His Val
        35                  40                  45

Thr Gly Lys Gly Val Thr Val Glu Thr Val Phe Ser Val Asp Glu Phe
    50                  55                  60
```

-continued

```
Ser Ala Ser Val Leu Thr Gly Lys Leu Thr Thr Val Phe Leu Pro Ile
65                  70                  75                  80

Val Tyr Thr Ile Val Phe Val Val Gly Leu Pro Ser Asn Gly Met Ala
                85                  90                  95

Leu Trp Val Phe Leu Phe Arg Thr Lys Lys Lys His Pro Ala Val Ile
            100                 105                 110

Tyr Met Ala Asn Leu Ala Leu Ala Asp Leu Leu Ser Val Ile Trp Phe
        115                 120                 125

Pro Leu Lys Ile Ala Tyr His Ile His Gly Asn Asn Trp Ile Tyr Gly
    130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Lys Ala Asn Ile Ala Ile
            180                 185                 190

Gly Ile Ser Leu Ala Ile Trp Leu Leu Ile Leu Leu Val Thr Ile Pro
        195                 200                 205

Leu Tyr Val Val Lys Gln Thr Ile Phe Ile Pro Ala Leu Asn Ile Thr
    210                 215                 220

Thr Cys His Asp Val Leu Pro Glu Gln Leu Leu Val Gly Asp Met Phe
225                 230                 235                 240

Asn Tyr Phe Leu Ser Leu Ala Ile Gly Val Phe Leu Phe Pro Ala Phe
                245                 250                 255

Leu Thr Ala Ser Ala Tyr Val Leu Met Ile Arg Met Leu Arg Ser Ser
            260                 265                 270

Ala Met Asp Glu Asn Ser Glu Lys Lys Arg Lys Arg Ala Ile Lys Leu
        275                 280                 285

Ile Val Thr Val Leu Ala Met Tyr Leu Ile Cys Phe Thr Pro Ser Asn
    290                 295                 300

Leu Leu Leu Val Val His Tyr Phe Leu Ile Lys Ser Gln Gly Gln Ser
305                 310                 315                 320

His Val Tyr Ala Leu Tyr Ile Val Ala Leu Cys Leu Ser Thr Leu Asn
                325                 330                 335

Ser Cys Ile Asp Pro Phe Val Tyr Tyr Phe Val Ser His Asp Phe Arg
            340                 345                 350

Asp His Ala Lys Asn Ala Leu Leu Cys Arg Ser Val Arg Thr Val Lys
        355                 360                 365

Gln Met Gln Val Ser Leu Thr Ser Lys Lys His Ser Arg Lys Ser Ser
    370                 375                 380

Ser Tyr Ser Ser Ser Ser Thr Thr Val Lys Thr Ser Tyr
385                 390                 395


<210> SEQ ID NO 3
<211> LENGTH: 8
<212> TYPE: PRT
<213> ORGANISM: Homo sapiens

<400> SEQUENCE: 3

Gly Gly Val Leu Val Gln Pro Gly
 1               5


<210> SEQ ID NO 4
<211> LENGTH: 6
<212> TYPE: PRT
```

-continued

<213> ORGANISM: Vibrio Cholerae phage CTXphi

<400> SEQUENCE: 4

```
Phe Cys Ile Gly Arg Leu
 1               5
```

<210> SEQ ID NO 5
<211> LENGTH: 14
<212> TYPE: PRT
<213> ORGANISM: Homo sapiens

<400> SEQUENCE: 5

```
Ser Leu Ile Gly Lys Val Asp Gly Thr Ser His Val Thr Gly
 1               5                   10
```

<210> SEQ ID NO 6
<211> LENGTH: 112
<212> TYPE: PRT
<213> ORGANISM: Vibrio Cholerae phage CTXphi

<400> SEQUENCE: 6

```
Phe Cys Ile Gly Arg Leu Cys Val Gln Asp Gly Phe Val Thr Val Gly
 1               5                   10                  15

Asp Glu Arg Tyr Arg Leu Val Asp Asn Leu Asp Ile Pro Tyr Arg Gly
            20                  25                  30

Leu Trp Ala Thr Gly His His Ile Tyr Lys Asp Thr Leu Thr Val Phe
        35                  40                  45

Phe Glu Thr Glu Ser Gly Ser Val Pro Thr Glu Leu Phe Ala Ser Ser
    50                  55                  60

Tyr Arg Tyr Lys Val Leu Pro Leu Pro Asp Phe Asn His Phe Val Val
65                  70                  75                  80

Phe Asp Thr Phe Ala Ala Gln Ala Leu Trp Val Glu Val Lys Arg Gly
                85                  90                  95

Leu Pro Ile Lys Thr Glu Asn Asp Lys Lys Gly Leu Asn Ser Ile Phe
            100                 105                 110
```

<210> SEQ ID NO 7
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi protein Zot oligopeptide
<220> FEATURE:
<221> NAME/KEY: VARIANT
<222> LOCATION: (1)...(1)
<223> OTHER INFORMATION: Xaa = Ala, Val, Leu, Ile, Pro, Trp, Tyr, or Met

<400> SEQUENCE: 7

```
Xaa Cys Ile Gly Arg Leu
 1               5
```

<210> SEQ ID NO 8
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi protein Zot oligopeptide
<220> FEATURE:
<221> NAME/KEY: VARIANT
<222> LOCATION: (2)...(2)
<223> OTHER INFORMATION: Xaa = Gly, Ser, Thr, Tyr, Asn, or Gln

<400> SEQUENCE: 8

-continued

```
Phe Xaa Ile Gly Arg Leu
 1               5


<210> SEQ ID NO 9
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (3)...(3)
<223> OTHER INFORMATION: Xaa = Ala, Val, Leu, Ile, Pro, Trp, or Met

<400> SEQUENCE: 9

Phe Cys Xaa Gly Arg Leu
 1               5


<210> SEQ ID NO 10
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (4)...(4)
<223> OTHER INFORMATION: Xaa = Gly, Ser, Thr, Tyr, Asn, Ala, or Gln

<400> SEQUENCE: 10

Phe Cys Ile Xaa Arg Leu
 1               5


<210> SEQ ID NO 11
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (5)...(5)
<223> OTHER INFORMATION: Xaa = Lys or His

<400> SEQUENCE: 11

Phe Cys Ile Gly Xaa Leu
 1               5


<210> SEQ ID NO 12
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (6)...(6)
<223> OTHER INFORMATION: Xaa = Ala, Val, Leu, Ile, Pro, Trp, or Met

<400> SEQUENCE: 12

Phe Cys Ile Gly Arg Xaa
 1               5


<210> SEQ ID NO 13
<211> LENGTH: 6
```

-continued

```
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (1)...(1)
<223> OTHER INFORMATION: Xaa = Ala, Val, Leu, Ile, Pro, Trp, Tyr, or Met
<220> FEATURE:
<221> NAME/KEY: VARIANT
<222> LOCATION: (2)...(2)
<223> OTHER INFORMATION: Xaa = Gly, Ser, Thr, Tyr, Asn, or Gn

<400> SEQUENCE: 13

Xaa Xaa Ile Gly Arg Leu
 1               5


<210> SEQ ID NO 14
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (1)...(1)
<223> OTHER INFORMATION: Xaa = Ala, Val, Leu, Ile, Pro, Trp, Tyr, or Met
<220> FEATURE:
<221> NAME/KEY: VARIANT
<222> LOCATION: (3)...(3)
<223> OTHER INFORMATION: Xaa = Ala, Val, Leu, Ile, Pro, Trp, or Met

<400> SEQUENCE: 14

Xaa Cys Xaa Gly Arg Leu
 1               5


<210> SEQ ID NO 15
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (1)...(1)
<223> OTHER INFORMATION: Xaa = Ala, Val, Leu, Ile, Pro, Trp,Tyr, or Met
<220> FEATURE:
<221> NAME/KEY: VARIANT
<222> LOCATION: (4)...(4)
<223> OTHER INFORMATION: Xaa = Gly, Ser, Thr, Tyr, Asn, Ala, or  Gln

<400> SEQUENCE: 15

Xaa Cys Ile Xaa Arg Leu
 1               5


<210> SEQ ID NO 16
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (1)...(1)
<223> OTHER INFORMATION: Xaa = Ala, Val, Leu, Ile, Pro, Trp, Tyr, or Met
<220> FEATURE:
<221> NAME/KEY: VARIANT
<222> LOCATION: (5)...(5)
<223> OTHER INFORMATION: Xaa = Lys or His
```

<400> SEQUENCE: 16

Xaa Cys Ile Gly Xaa Leu
 1 5

<210> SEQ ID NO 17
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
 protein Zot oligopeptide
<220> FEATURE:
<221> NAME/KEY: VARIANT
<222> LOCATION: (1)...(1)
<223> OTHER INFORMATION: Xaa = Ala, Val, Leu, Ile, Pro, Trp,Tyr, or Met
<220> FEATURE:
<221> NAME/KEY: VARIANT
<222> LOCATION: (6)...(6)
<223> OTHER INFORMATION: Xaa = Ala, Val, Leu, Ile, Pro, Trp, or Met

<400> SEQUENCE: 17

Xaa Cys Ile Gly Arg Xaa
 1 5

<210> SEQ ID NO 18
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
 protein Zot oligopeptide
<220> FEATURE:
<221> NAME/KEY: VARIANT
<222> LOCATION: (2)...(2)
<223> OTHER INFORMATION: Xaa = Gly, Ser, Thr, Tyr, Asn, or Gln
<220> FEATURE:
<221> NAME/KEY: VARIANT
<222> LOCATION: (3)...(3)
<223> OTHER INFORMATION: Xaa = Ala, Val, Leu, Ile, Pro, Trp, or Met

<400> SEQUENCE: 18

Phe Xaa Xaa Gly Arg Leu
 1 5

<210> SEQ ID NO 19
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
 protein Zot oligopeptide
<220> FEATURE:
<221> NAME/KEY: VARIANT
<222> LOCATION: (2)...(2)
<223> OTHER INFORMATION: Xaa = Gly, Ser, Thr, Tyr, Asn, or Gln
<220> FEATURE:
<221> NAME/KEY: VARIANT
<222> LOCATION: (4)...(4)
<223> OTHER INFORMATION: Var = Gly, Ser, Thr, Tyr, Asn, Ala, or Gln

<400> SEQUENCE: 19

Phe Xaa Ile Xaa Arg Leu
 1 5

<210> SEQ ID NO 20
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi

```
      protein Zot oligopeptide
<220> FEATURE:
<221> NAME/KEY: VARIANT
<222> LOCATION: (2)...(2)
<223> OTHER INFORMATION: Xaa = Gly, Ser, Thr, Tyr, Asn, or Gln
<220> FEATURE:
<221> NAME/KEY: VARIANT
<222> LOCATION: (5)...(5)
<223> OTHER INFORMATION: Xaa = Lys or His

<400> SEQUENCE: 20

Phe Xaa Ile Gly Xaa Leu
 1               5


<210> SEQ ID NO 21
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (2)...(2)
<223> OTHER INFORMATION: Xaa = Gly, Ser, Thr, Tyr, Asn, or Gln
<220> FEATURE:
<221> NAME/KEY: VARIANT
<222> LOCATION: (6)...(6)
<223> OTHER INFORMATION: Xaa = Ala, Val, Leu, Ile, Pro, Trp, or Met

<400> SEQUENCE: 21

Phe Xaa Ile Gly Arg Xaa
 1               5


<210> SEQ ID NO 22
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (3)...(3)
<223> OTHER INFORMATION: Xaa = Ala, Val, Leu, Ile, Pro, Trp, or Met
<220> FEATURE:
<221> NAME/KEY: VARIANT
<222> LOCATION: (4)...(4)
<223> OTHER INFORMATION: Xaa = Gly, Ser, Thr, Tyr, Asn, Ala, or Gln

<400> SEQUENCE: 22

Phe Cys Xaa Xaa Arg Leu
 1               5


<210> SEQ ID NO 23
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (3)...(3)
<223> OTHER INFORMATION: Xaa = Ala, Val, Leu, Ile, Pro, Trp, or Met
<220> FEATURE:
<221> NAME/KEY: VARIANT
<222> LOCATION: (5)...(5)
<223> OTHER INFORMATION: Xaa = Lys or His

<400> SEQUENCE: 23

Phe Cys Xaa Gly Xaa Leu
```

-continued

```
 1               5


<210> SEQ ID NO 24
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (3)...(3)
<223> OTHER INFORMATION: Xaa = Ala, Val, Leu, Ile, Pro, Trp, or Met
<220> FEATURE:
<221> NAME/KEY: VARIANT
<222> LOCATION: (6)...(6)
<223> OTHER INFORMATION: Xaa = Ala, Val, Leu, Ile, Pro, Trp, or Met

<400> SEQUENCE: 24

Phe Cys Xaa Gly Arg Xaa
 1               5


<210> SEQ ID NO 25
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (4)...(4)
<223> OTHER INFORMATION: Xaa = Gly, Ser, Thr, Tyr, Asn, Ala, or Gln
<220> FEATURE:
<221> NAME/KEY: VARIANT
<222> LOCATION: (5)...(5)
<223> OTHER INFORMATION: Xaa = Lys or His

<400> SEQUENCE: 25

Phe Cys Ile Xaa Xaa Leu
 1               5


<210> SEQ ID NO 26
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (4)...(4)
<223> OTHER INFORMATION: Xaa = Gly, Ser, Thr, Tyr, Asn, Ala, or Gln
<220> FEATURE:
<221> NAME/KEY: VARIANT
<222> LOCATION: (6)...(6)
<223> OTHER INFORMATION: Xaa = Ala, Val, Leu, Ile, Pro, Trp, or Met

<400> SEQUENCE: 26

Phe Cys Ile Xaa Arg Xaa
 1               5


<210> SEQ ID NO 27
<211> LENGTH: 6
<212> TYPE: PRT
<213> ORGANISM: Artificial Sequence
<220> FEATURE:
<223> OTHER INFORMATION: susbstition mutant of Vibrio cholerae CXTphi
      protein Zot oligopeptide
<220> FEATURE:
<221> NAME/KEY: VARIANT
<222> LOCATION: (5)...(5)
```

-continued

```
<223> OTHER INFORMATION: Xaa = Lys or His
<220> FEATURE:
<221> NAME/KEY: VARIANT
<222> LOCATION: (6)...(6)
<223> OTHER INFORMATION: Xaa = Ala, Val, Leu, Ile, Pro, Trp, or Met

<400> SEQUENCE: 27

Phe Cys Ile Gly Xaa Xaa
 1               5
```